(12) United States Patent
Hotz et al.

(10) Patent No.: US 8,828,365 B2
(45) Date of Patent: Sep. 9, 2014

(54) ADDITIVE FOR UV-SUNSCREEN PREPARATIONS

(75) Inventors: Jutta Hotz, Zürich (CH); Ulrich Huber, Erlenbach (CH); Volker Schehlmann, Schopfheim (DE); Daniel Sprenger, Basel (CH)

(73) Assignee: DSM IP Assets B.V., Heerlen (NL)

( * ) Notice: Subject to any disclaimer, the term of this patent is extended or adjusted under 35 U.S.C. 154(b) by 1193 days.

(21) Appl. No.: 11/666,666

(22) PCT Filed: Oct. 26, 2005

(86) PCT No.: PCT/EP2005/011458
§ 371 (c)(1),
(2), (4) Date: May 23, 2007

(87) PCT Pub. No.: WO2006/048159
PCT Pub. Date: May 11, 2006

(65) Prior Publication Data
US 2008/0089852 A1   Apr. 17, 2008

(30) Foreign Application Priority Data
Nov. 2, 2004   (EP) .................................... 04025930

(51) Int. Cl.
*A61Q 17/04* (2006.01)
*A61K 8/18* (2006.01)
*A61K 8/72* (2006.01)
*A61K 8/81* (2006.01)
*C08F 220/36* (2006.01)
*C08F 212/08* (2006.01)

(52) U.S. Cl.
CPC ........... *A61K 8/8111* (2013.01); *A61K 2800/57* (2013.01); *A61K 8/8147* (2013.01); *A61Q 17/04* (2013.01); *C08F 220/36* (2013.01); *A61K 8/8117* (2013.01); *C08F 212/08* (2013.01)
USPC ............................... 424/60; 424/59; 523/105

(58) Field of Classification Search
None
See application file for complete search history.

(56) References Cited

U.S. PATENT DOCUMENTS

| 4,115,348 | A | * | 9/1978 | Wang et al. | ..................... 524/95 |
| 4,233,430 | A | * | 11/1980 | Jacquet et al. | ................. 526/259 |
| 6,123,928 | A | * | 9/2000 | Sovak et al. | ..................... 424/59 |
| 2006/0159637 | A1 | | 7/2006 | Meyer et al. | |

FOREIGN PATENT DOCUMENTS

| CA | 2 531 556 | 6/2006 |
| GB | 1 579 647 | 11/1980 |
| GB | 2 185 396 | 7/1987 |
| JP | 7-291845 | 11/1995 |
| WO | WO 03068183 A1 * | 8/2003 |
| WO | 2004/007592 | 1/2004 |
| WO | WO 2005/053631 A1 | 6/2005 |

OTHER PUBLICATIONS

Varma et al; Beilstein, Jun. 27, 1998, XP-002327224.
International Search Report mailed Feb. 2, 2006 in PCT/EP2005/011458.
Written Opinion mailed Feb. 2, 2006 in PCT/EP2005/011458.

* cited by examiner

*Primary Examiner* — Brian-Yong Kwon
*Assistant Examiner* — Jennifer A Berrios
(74) *Attorney, Agent, or Firm* — Nixon & Vanderhye P.C.

(57) ABSTRACT

The invention relates to the use of polymeric particles for boosting the UV absorption of an UV filter in an UV-sunscreen composition, wherein the polymeric particles comprise at least one polymeric particle comprising at least one chromophore having an UV absorption maximum at $\lambda_{max} \geq 275$ nm covalently bound thereto.

6 Claims, No Drawings

ADDITIVE FOR UV-SUNSCREEN PREPARATIONS

This application is the US national phase of international application PCT/EP2005/011458 filed 26 Oct. 2005 which designated the U.S. and claims benefit of EP 04025930.1, dated 2 Nov. 2004, the entire content of which is hereby incorporated by reference.

The present invention relates to polymeric particles which are useful as additives in UV-sunscreen preparations, i.e. in compositions for the protection of the human skin and/or hair against harmful effects of sunlight. The polymeric particles boost the absorption of the UV filters which act as sunscreens.

There is a constantly increasing need for sunscreen protection agents in a population which is exposed to an increasing amount of damaging sunlight. Repetitive sun exposure can result in skin changes known as photoaged skin. The clinical changes that are seen in photoaged skin differ from those of normally aged skin in the sites of the body protected against sunlight. Among damaging results of extensive sun exposure of the skin there is increased wrinkling, elastosis, pigmentary changes, precancerous and cancerous skin lesions.

Many sunscreen chemicals have been developed in the past protecting against the harmful effect of UV-A (320 nm to 400 nm) and/or UV-B (290 nm to 320 nm) wavelength and even shorter wavelength (UV-C). These UV filters are usually incorporated either alone or in combination with each other into cosmetic or pharmaceutical preparations which are widely known and used.

However, the properties of the UV sunscreen formulations known from the prior art are not satisfactory in every respect.

For example, when applied to the skin, many sunscreen formulations of the prior art have a shiny appearance and do not properly smoothen and flatten the skin. Some sunscreen formulations suffer from poor rheological properties and therefore require the addition of thickeners or viscosity adjusting ingredients. Other sunscreen formulations only show a limited adhesion on hair and skin. In certain cases fragrances contained in the formulations are rapidly released such that no sustained release of the fragrances can be achieved.

The effectiveness of a sunscreen formulation is generally assessed by how well it protects the skin in terms of a Sun Protection Factor (SPF) which is defined as the ratio of the amount of energy required to produce a minimal erythema on sunscreen protected skin to the amount of energy required to produce the same level of erythema on unprotected skin.

Besides a high SPF, a good UV absorbing chromophore should have excellent photostability, toxicological and dermatological acceptability, excellent heat stability, very good solubility in cosmetic solvents, in particular in oil or water, compatibility with cosmetic bases, pH stability in the range of 4 to 9, processability into cosmetic formulations, compatibility with other ingredients of cosmetic formulations and with the packaging materials, no staining of textiles, it should be free of color and of neutral or pleasant odor, and it should be free of tackiness and have a low volatility.

A high SPF-value could theoretically be achieved by increasing the amount of chromophores in the sunscreen formulation or by using chromophores providing a higher SPF-value. However, problems can occur in both cases.

For example, a number of UV radiation absorbing agents, typically used in sunscreen formulations have adverse toxicological or irritating effects. For safety reasons, the concentration of those agents should be kept as low as possible. Increasing the amount of chromophores can also cause problems with the stability of the sunscreen agent and restricts the number of suitable adjuvants which can be used for stabilizing the compositions.

One attempt to reduce the level of UV radiation absorbing agents in a sunscreen formulation is described in U.S. Pat. No. 5,663,213 disclosing that voided latex particles having certain particle sizes, increase the absorption of UV radiation in a composition containing one or more UV radiation absorbing agents. These voided latex particles act as boosters of the UV filter compounds which are present in the sunscreen composition.

Polymer latices having UV absorbing chromophores (UV filters) covalently bound to the polymer and their use in cosmetic compositions are known from the prior art. In this regard it can be referred to e.g. JP-A 02 091109, JP-A 03 220213, JP-A 05 039327, JP-A 05 065316 and JP-A 05 255655. The polymer particles are composed of polymers in which monomers having an UV-chromophore are covalently bound to co-monomers without such chromophores.

It is an object of the present invention to provide sunscreen formulations which do not have the problems of the prior art sunscreen formulations, which are safe in use and nevertheless exhibit a high sun protection factor.

This technical problem is solved by the subject matter of the claims.

It has been surprisingly found that the UV absorption of UV filters contained in sunscreen compositions can be boosted, i.e. enhanced by means of polymeric particles obtained from emulsion polymerization of an ethylenically unsaturated monomer and one or more co-monomers capable of reacting with said ethylenically unsaturated monomer. The emulsion polymerization provides a latex containing the polymeric particles.

The latex and the polymeric particles of the present invention may be included into cosmetic compositions as additives. The resulting sunscreen compositions have several advantages over the sunscreen compositions of the prior art. For example, the polymeric particles increase the optical distance of the sunlight through the sunscreen composition by scattering the light thereby increasing the efficiency of the sunscreen agents contained in the composition. In this respect, the polymeric particles of the present invention act as boosters for UV sunscreens. The polymeric particles decrease the amount of sunlight reaching the skin by scattering and reflecting the sunlight. They may reduce the shininess and may transfer it to a velvet-like appearance of the skin and smoothen and flatten the skin. They may exhibit a thickening effect and are useful as viscosity adjusting agents. They may improve the adhesion of the composition on hair and skin. Unexpectedly, the polymeric particles can also be used in an UV-sunscreen composition for beautifying and/or rejuvenating the skin.

The polymeric particles can also be used as rheology modifier, soft focus enhancer for skin improvement and as no skin delivery capsules.

The present invention relates to the use of polymeric particles for boosting the UV absorption of an UV filter in an UV-sunscreen composition, wherein the polymeric particles comprise at least one polymeric particle comprising at least one chromophore having an UV absorption maximum at $\lambda_{max} \geq 275$ nm covalently bound thereto.

Preferably, each polymeric particle is covalently bound to at least one chromophore such that there are no polymeric particles which are not covalently bound to a chromophore.

Preferably, $\lambda_{max} \geq 280$ nm, more preferably $\geq 285$ nm, still more preferably $\geq 290$ nm, yet more preferably $\geq 295$ nm, most preferably $\geq 300$ nm and in particular $\geq 305$ nm.

For the purpose of the specification "UV absorption maximum" means a local absorption maximum within the range of from 275 to 400 nm. In case that the chromophore exhibits more than one maximum within said range, preferably the maximum having the highest extinction coefficient is relevant for the above definition.

Preferably, the UV absorption maximum of a chromophore is determined in THF or Dioxane or another suitable solvent.

In the polymeric particles according to the invention the chromophore may preferably be represented by any group which absorbs light in the range of wavelengths 400 nm to 320 nm (UV-A) and 320 nm to 290 nm (UV-B) or of even shorter wavelengths (UV-C) but ≥275 nm. These groups are, e.g., residues of compounds belonging to the groups of acrylates, p-aminobenzoates, camphor derivatives, cinnamates, benzophenones, benzalmalonic acid esters, 2-(4-ethoxy anilinomethylene)-propandioic esters, imidazole derivatives, salicylates, triazone derivatives, benzotriazol derivatives, dibenzoylmethanes, amino substituted hydroxybenzophenones, phenyl-benzimidazoles, anthranilates, phenyl-benzoxazoles, 1,4-dihydropyranes and 1,4-dihydropyridine derivatives and others representing state of the art and known to those skilled in the art to be highly active.

Preferred UV absorbing chromophores are a) dihydropyridine derivatives such as

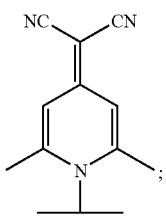
;

b) benzoxazole derivatives such as

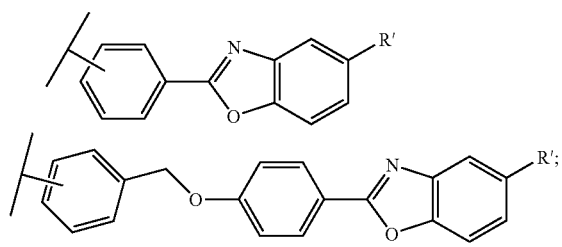
;

c) benzimidazole derivatives such as

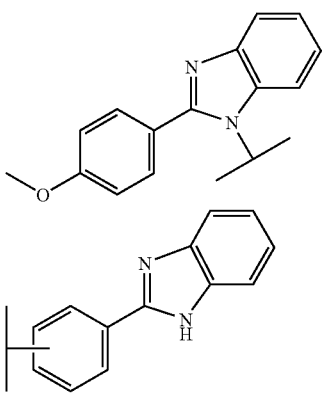

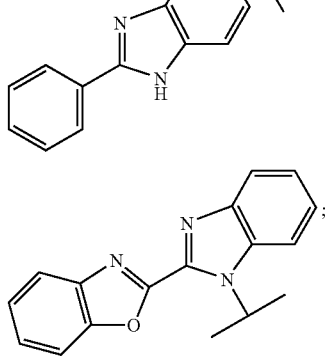
;

d) benzotriazol derivatives such as

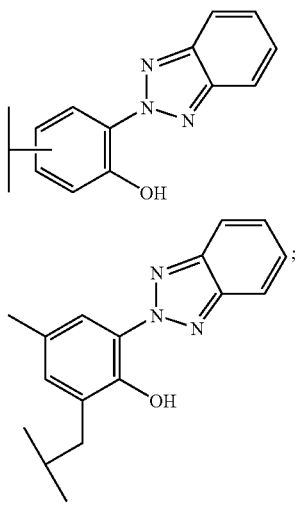
;

e) benzophenone derivatives such as

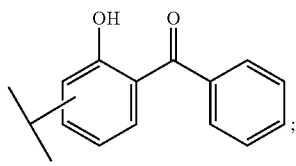
;

f) p-aminobenzoic acid derivatives such as

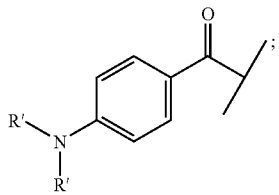
;

g) camphor derivatives such as

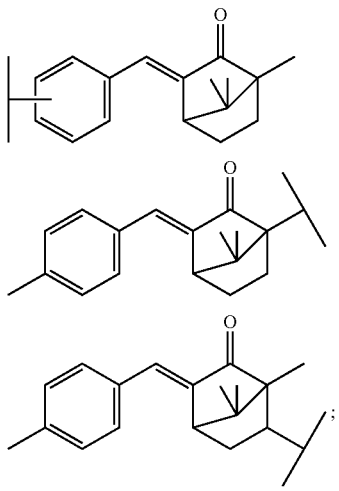

h) cinnamic acid or benzalmalonate derivatives such as

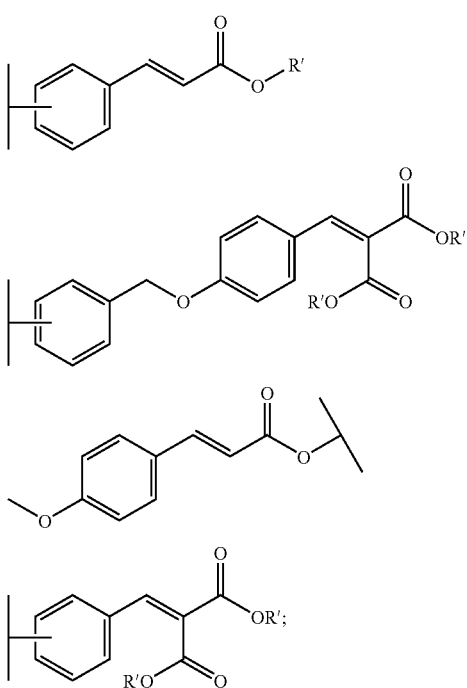

i) octocrylene derivatives such as

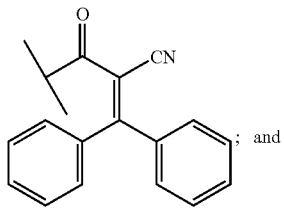 [SMILES: CC(C)C(=O)C(C#N)=C(c1ccccc1)c1ccccc1]; and j) tert-butyldibenzoylmethane derivatives such as

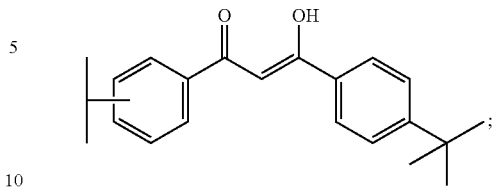

wherein R' is —H, —OH, —$C_1$-$C_{20}$-alkyl, —$C_1$-$C_{20}$-alkoxy or —$C_{2-20}$-alkenyl and "⊣" denotes the linkage to the polymeric particles.

In a preferred embodiment of the present invention the chromophore comprises a moiety according to general formula (I)

wherein
Q is a 5- or 6-membered heterocyclic ring including 1, 2, 3 or 4 heteroatoms independently selected from N, O and S, said heterocyclic ring
(i) optionally being substituted with 1, 2, 3 or 4 residues defined as $R^1$, $R^2$, $R^3$ and $R^4$; and/or
(ii) optionally being annealed to a phenyl ring substituted with $R^5$, $R^6$, $R^7$ and $R^8$;
$Y^1$ and $Y^2$ are independently —O—, —CO—; —$CO_2$—; —OCO—; —NR'CO— wherein R' is —H or —$C_1$-$C_6$-alkyl; —$C_1$-$C_6$-alkylene-; or -phenylene- substituted with $R^9$, $R^{10}$, $R^{11}$ and $R^{12}$;
T is —O—; —S—; or —NR"— wherein R" is —H or —$C_1$-$C_6$-alkyl;
L is a linker unit;
wherein
$R^1$, $R^2$, $R^3$, $R^4$, $R^5$, $R^6$, $R^7$, $R^8$, $R^9$, $R^{10}$, $R^{11}$ and $R^{12}$ are independently selected from —H, —F, —Cl, —CN, —$CF_3$, —$N_3$, —NO, —$NO_2$, —OH, —OCO—$C_1$-$C_6$-alkyl, —$CO_2H$, —$SO_3H$, —$CO_2$—$C_1$-$C_6$-alkyl, —S(O)$_k$—$C_1$-$C_6$-alkyl wherein index k is 0, 1 or 2, —CO—$C_1$-$C_6$-alkyl, —$NH_2$, —NH—$C_1$-$C_6$-alkyl, —N($C_1$-$C_6$-alkyl)$_2$, —NHCO—$C_1$-$C_6$-alkyl, —$C_1$-$C_{20}$-alkyl wherein optionally 1, 2 or 3 methylene groups are replaced by —O—, —$C_3$-$C_7$-cycloalkyl, methenyl (optionally substituted with $R^a$ and $R^b$ independently selected from —Cl, —CN, —$CO_2$—$C_1$-$C_6$-alkyl and —O—$C_1$-$C_6$-alkyl), —$C_2$-$C_{20}$-alkenyl, —$C_2$-$C_{20}$-alkynyl, —$C_6$-$C_{10}$-aryl, —$C_3$-$C_9$-heteroaryl, —$C_7$-$C_{20}$-alkylaryl wherein optionally 1, 2 or 3 methylene groups are replaced by —O—, —CO— $C_6$-$C_{10}$-aryl or —$C_5$-$C_{20}$-alkylheteroaryl
index l is 0 or 1;
index m is 0 or 1;
index n is an integer of 0 to 10, preferably 0, 1 or 2; and
⊣ denotes the covalent bond to the polymeric particles.

Preferably, Q is an aromatic ring.
Preferably, Q is a 5- or 6-membered heterocyclic ring including 1 or 2 heteroatoms independently selected from N and O, which is optionally substituted with 1, 2, 3 or 4 residues defined as $R^1$, $R^2$, $R^3$ and $R^4$ and/or optionally annealed to a phenyl ring substituted with $R^5$, $R^6$, $R^7$ and $R^8$.

When any of $R^1$ to $R^{12}$ is methenyl (optionally substituted with $R^a$ and $R^b$ independently selected from —Cl, —CN, —$CO_2$—$C_1$-$C_6$-alkyl and —O—$C_1$-$C_6$-alkyl), there is a double bond between the carbon atom of the methenyl group and the 5- or 6-membered heterocyclic ring ($R^1$ to $R^4$), the annealed phenyl ring ($R^5$ to $R^8$) and the substituted phenylene ring ($R^9$ to $R^{12}$), respectively. This may cause the heterocyclic ring, the phenyl ring and the phenylene ring to form a chinoid aromatic system. For example, when the heterocyclic ring is derived from pyridine and the substituent in 4-position is a methenyl group substituted with two cyano residues ($R^a$ and $R^b$), two of the π-bonds are in 2,3- and 5,6-position, respectively, and the third double bond is the exocyclic bond to the carbon atom of the methenyl group. Preferably, only one of $R^1$ to $R^{12}$ may be a methenyl group.

The linker unit L is not particularly restricted, and any suitable linker unit can be used. Preferably L is a group with the general formula $-(B)_b(C)_c(D)_d(E)_e-$ wherein B is —$C_1$-$C_{20}$-alkylene-, preferably —$C_1$-$C_{12}$-alkylene-, most preferably —$C_3$-$C_{12}$-alkylene-, wherein each carbon atom might additionally bear a hydroxy substituent;

C is —O—, —S— or —NH—;

D is —CONH—;

E is —$C_1$-$C_{20}$-alkylene- or —$C_2$-$C_{20}$-alkenylene-, preferably —$C_1$-$C_{12}$-alkylene- or —$C_2$-$C_{12}$-alkenylene-, most preferably —$C_3$-$C_{12}$-alkylene- or —$C_3$-$C_{12}$-alkenylene-, and b, c, d and e are independently 0 or 1;

wherein each alkylene group can be unsubstituted or substituted, preferably with 1 or 2 substituents, preferably —OH, and wherein b+c+d+e is not 0.

The linker unit in total has preferably 1 to 10 carbon atoms and optionally 1 to 3 hetero atoms such as nitrogen or oxygen atoms and is preferably of the formula $-(B)_b(C)_c(D)_d(E)_e-$ as defined above.

Preferably, index n is 1 or 2 and L is —$C_2$-$C_6$-alkylene-O— or —$C_2$-$C_6$-alkylene-NH— wherein the carbon atoms of the alkylene-groups may be optionally substituted with one, two or three hydroxy groups. In another preferred embodiment index n is 0.

If n≠0, the linker unit L is most preferably —$C_2$-$C_6$-alkylene-O— or —$C_2$-$C_6$-alkylene-NH— wherein the carbon atoms of the alkylene-chain may be optionally substituted with one, two or three hydroxy groups. More preferably, the linker unit L is selected from the group consisting of —$CH_2CH_2$—O—, —$CH(CH_3)CH_2$—O—, —$CH_2CH(CH_3)$—O—, —$CH_2$—CH(OH)—$CH_2$—O— and —$CH_2CH_2$—NH—. Index n is preferably 1, 2, 3 or 4. It is also preferred that index n is zero.

In a preferred embodiment the chromophore comprises a moiety according to general formula (II)

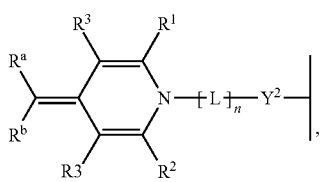

(II)

wherein $R^1$, $R^2$, $R^3$, $R^a$, $R^b$, L, $Y^2$ and n are defined as above.

In the moiety according to general formula (II)

$R^a$ and $R^b$ are preferably —CN;

$R^1$ and $R^2$ are preferably —$C_1$-$C_6$-alkyl, more preferably independently selected from —$CH_3$, —$CH_2CH_3$, —$CH(CH_3)_2$ and —$C(CH_3)_3$, most preferably —$CH_3$;

$R^3$ is preferably —H;

L is —$CH_2CH_2O$— such that the terminal carbon atom is bound to the nitrogen atom of the pyridine and the terminal oxygen atom is bound to $Y^2$;

index n is 1 or 2; and $Y^2$ is —CO—.

In another preferred embodiment of the present invention the chromophore comprises a moiety according to general formula (III)

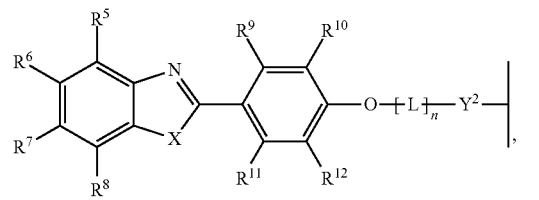

(III)

wherein $R^5$, $R^6$, $R^7$, $R^8$, $R^9$, $R^{10}$, $R^{11}$, $R^{12}$, L, $Y^2$ and n are defined as above, and X is —S—, —O— or —NR'''— (wherein R''' is —H or —$C_1$-$C_{20}$-alkyl).

Preferably, in the moiety according to general formula (III) X is —O— or —NR'''— (wherein R''' is —H or —$C_1$-$C_{20}$-alkyl); and $R^5$, $R^6$, $R^7$ and $R^8$ are independently —H, —CN, —$NO_2$, —OH, —$NH_2$, —NH—$C_1$-$C_6$-alkyl, —N($C_1$-$C_6$-alkyl)$_2$, —$C_5$-$C_{10}$-aryl or —$C_1$-$C_{20}$-alkyl (wherein optionally 1, 2 or 3 methylene groups may be replaced by —O—), more preferably —H or —$C_1$-$C_6$-alkyl.

Preferably only one or two of the residues $R^5$ to $R^8$, more preferably only one of these residues is different from —H. Most preferably, $R^5$ and $R^8$, still more preferably $R^5$, $R^7$ and $R^8$ are —H.

Preferably, $R^9$, $R^{10}$, $R^{11}$ and $R^{12}$ are independently selected from —H, —F, —Cl, —OH, —$C_1$-$C_6$-alkyl and —$C_1$-$C_6$-alkoxy, most preferably $R^9$, $R^{10}$, $R^{11}$ and $R^{12}$ are —H.

More preferably, in the moiety according to general formula (III)

X is —O—;

$R^5$, $R^7$ and $R^8$ are —H;

$R^6$ is —H or —$C_1$-$C_6$-alkyl, most preferably selected from the group consisting of —H, —$CH_3$, —$CH_2CH_3$, —$CH(CH_3)_2$, —$C(CH_3)_3$ and —$C(CH_3)_2CH_2CH_3$;

$R^9$, $R^{10}$, $R^{11}$ and $R^{12}$ are —H;

L is —$C_1$-$C_6$-alkylene- optionally substituted with a residue —OH, most preferably selected from —$CH_2$—, —$CH_2CH_2O$— and —$CH_2CH(OH)CH_2$—;

index n is 0, 1 or 2; and $Y^2$ is —CO—, —OCO— or -phenylene-.

For the purpose of the present specification (meth)acrylic means either methacrylic or acrylic;

—$C_1$-$C_6$-alkyl means methyl or —$C_2$-$C_6$-alkyl;

—$C_2$-$C_6$-alkyl means straight or branched alkyl such as ethyl, n-propyl, iso-propyl, n-butyl, iso-butyl, sec-butyl, tert-butyl, n-pentyl, iso-pentyl, neo-pentyl, n-hexyl or iso-hexyl;

—$C_1$-$C_6$-alkylene means straight or branched alkylene such as —$CH_2$—, $CH_2CH_2$—, —$CH_2CH_2$—$CH_2$—, —$CH(CH_3)CH_2$—, —$CH_2CH(CH_3)$— and —$CH_2CH_2CH_2CH_2$—;

—OCO—$C_1$-$C_6$-alkyl is preferably —OCO—$CH_3$ or —OCO—$CH_2CH_3$;

—$CO_2$—$C_1$-$C_6$-alkyl is preferably —$CO_2$—$CH_3$ or —$CO_2$—$CH_2CH_3$;

—$S(O)_m$—$C_1$-$C_6$-alkyl (wherein index m is 0, 1 or 2) is preferably —S—$CH_3$, —S—$CH_2CH_3$, —$SO_2$—$CH_3$ or —$SO_2$—$CH_2CH_3$;

—CO—$C_1$-$C_6$-alkyl is preferably —CO—$CH_3$ or —CO—$CH_2CH_3$;
—NH—$C_1$-$C_6$-alkyl is preferably —NH—$CH_3$ or —NH—$CH_2CH_3$;
—N($C_1$-$C_6$-alkyl)$_2$ is preferably —N($CH_3$)$_2$ or —N($CH_2CH_3$)$_2$;
—NHCO—$C_1$-$C_6$-alkyl is preferably —NHCO—$CH_3$ or —NHCO—$CH_2CH_3$;
—$C_1$-$C_{20}$-alkyl (wherein optionally up to three methylene groups (i.e. 1, 2 or 3 methylene groups) may be replaced by —O—) means straight or branched alkyl such as —$C_1$-$C_6$-alkyl, heptyl, octyl, nonyl, decyl, undecyl, dodecyl, tridecyl, tetradecyl, pentadecyl, hexadecyl, heptadecyl, octadecyl, nonadecyl and eicosyl; straight or branched —$C_1$-$C_{19}$-alkoxy such as —O—$C_1$-$C_6$-alkyl; or various straight or branched alkylether such as —$C_2$-$C_6$-alkyl-O—$C_1$-$C_6$-alkyl, —O—$C_2$-$C_6$-alkyl-O—$C_1$-$C_6$-alkyl, —$C_2$-$C_6$-alkyl-O—$C_2$-$C_6$-alkyl-O—$C_1$-$C_6$-alkyl, —O—$C_2$-$C_6$-alkyl-O—$C_2$-$C_6$-alkyl-O—$C_1$-$C_5$-alkyl;
—$C_3$-$C_7$-cycloalkyl is preferably cyclopropyl, cyclobutyl, cyclopentyl or cycloheptyl;
—$C_2$-$C_{20}$-alkenyl means straight or branched alkenyl such as —CH=$CH_2$ or —$CH_2$CH=$CH_2$;
—$C_2$-$C_{20}$-alkynyl means straight or branched alkynyl such as —C≡CH or —$CH_2$C≡CH;
—$C_5$-$C_{10}$-aryl is preferably phenyl or naphthyl;
—$C_3$-$C_9$-heteroaryl means a 5- to 7-membered aromatic ring having 1 to 4 heteroatoms independently selected from N, O and S and optionally annealed with another 5- to 7-membered aromatic or aliphatic ring optionally having 1 to 3 heteroatoms independently selected from N, O and S, such as pyridyl, pyrrolyl, furyl, thienyl and indolyl;
—$C_6$-$C_{20}$-alkylaryl (wherein optionally up to three methylene groups may be replaced by —O—) is preferably —$C_1$-$C_6$-alkyl-$C_5$-$C_{10}$-aryl, such as —$CH_2$—$C_6H_5$, —$CH_2CH_2$—$C_6H_5$, —O—$CH_2$—$C_6H_5$ and —$CH_2CH_2$—O—$C_6H_5$;
—CO—$C_5$-$C_{10}$-aryl is preferably —CO—$C_6H_5$; and
—$C_5$-$C_{20}$-alkylheteroaryl is preferably —$C_1$-$C_6$-alkyl-$C_3$-$C_9$-heteroaryl.

The present invention also relates to a process for the preparation of polymeric particles as described above, wherein an ethylenically unsaturated monomer represented by general formula (IV)

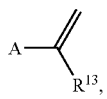

(IV)

wherein
$R^{13}$ is —H or —$C_1$-$C_6$-alkyl, preferably —H or —$CH_3$; and
A is a moiety according to any of general formulae (I), (II) and (III) as described above;
and one or more co-monomers capable of reacting with the ethylenically unsaturated monomer of general formula (IV) are subjected to an emulsion polymerization. Preferably, A is a moiety represented by general formula (II) or general formula (III) as defined above.

In a preferred embodiment of the process according to the invention the one or more co-monomers comprise co-monomers selected from the group consisting of (meth)acrylic acid, (meth)acrylic acid $C_1$-$C_{20}$-alkylester and styrene.

Preferably, the process comprises the further step of adding a hydrophilic compound to the ethylenically unsaturated monomer of general formula (IV) and the one or more co-monomers either before the polymerization is started, or during the polymerization process, or after the polymerization is finished, the hydrophilic compound being selected from the group consisting of polyethylene glycol, polypropylene glycol, ethylene glycol, glycerol, DMF and cyclodextrin.

The polymerization step of the process according to the present invention is performed in emulsion. In contrast to other conventional polymerization processes, the emulsion polymerization is a heterogeneous reaction process. The water insoluble mixture of monomers is emulsified in the aqueous phase (continuous phase) with the aid of an emulsifier. The polymerization reaction is started with an initiator, and the polymerization results in a colloidal dispersion, called "latex". The particles of the latex are principally spheres, and the diameter of the particles is usually within in the range of from 0.01 μm to 5 μm preferably 0.1 μm to 3 μm and depending on their average size the particles are also called "nanoparticles" and "microparticles", respectively. The diameter of the polymeric particles is usually much smaller than the diameter of the original emulsion droplets forming the latex.

Preferably, at least one emulsifier is added to the reaction mixture. The skilled person is aware of suitable emulsifiers. Preferred emulsifiers are sodium dodecylsulfate (SDS), sodium laurylsulfate (SLS), Tween 80 (polyoxyethylene sorbitan monooleate), polyethylene glycol 400 and mixtures thereof.

Preferably, the one or more co-monomers act as solvent for the ethylenically unsaturated monomer of general formula (IV). Preferably, the solution contains up to 30 wt.-% or even more of the ethylenically unsaturated monomer of general formula (IV), preferably in the presence of one or more emulsifiers.

It has been surprisingly found that co-monomers with specific chromophores having a sufficiently high extinction coefficient are reasonably soluble in copolymerizable co-monomer(s) not carrying a chromophore and surprisingly are sufficiently incorporated into the polymer to provide a latex and polymeric particles having a very high extinction coefficient. Thus, said specific co-monomers with chromophores provide an excellent balance between a high extinction coefficient, good solubility in the co-monomer(s) and good ability of being incorporated into the polymer (e.g. covalently bound to the polymer).

Preferably, the monomers are pre-emulsified before the polymerization is started.

Preferably, the polymerization is a radical reaction which is initiated by a radical initiator. Suitable radical initiators are known to the person skilled in the art. Preferably, the radical initiator is soluble in water. Sodium peroxydisulfate ($Na_2S_2O_8$) is most preferred. The initiator may be added to the reaction mixture continuously, dropwise, stepwise, etc.

Preferably the emulsion polymerization is performed at a temperature between 10 and 100° C., more preferably between 20 and 95° C., most preferably between 30 and 90° C., in particular between 50 and 90° C.

In a preferred embodiment of the process according to the invention the emulsion polymerization is performed by mixing the following components:
an emulsion of a lipid phase containing a mixture of the ethylenically unsaturated monomer of general formula (IV) and the one or more co-monomers;
an aqueous phase; and
at least one initiator.

Preferably, the process according to the invention comprises the steps of:
- dissolving the ethylenically unsaturated monomer of general formula (IV) in the one or more co-monomers;
- emulsifying the resulting solution with 50 to 300 vol.-% of water based on the volume of the solution;
- initiating the polymerization by adding an initiator.

Preferably, the mixture of the ethylenically unsaturated monomer of general formula (IV) and the one or more co-monomers contains 10 to 70 wt.-%, more preferably 15 to 60 wt.-% of the ethylenically unsaturated monomer of general formula (IV). Preferably, the emulsion is added to the aqueous phase at a temperature of 30 to 90° C., more preferably 50 to 90° C.

Preferably, the weight average molecular weight $M_w$ of the polymer obtained from the polymerization of the ethylenically unsaturated monomer of general formula (IV) and the one or more co-monomers is within the range of from 5,000 to 500,000 gmol$^{-1}$, more preferably from 10,000 to 250,000 gmol$^{-1}$, most preferably from 15,000 to 150,000 gmol$^{-1}$.

A chain transfer agent may be added to the reaction mixture. Suitable chain transfer agents are known to the person skilled in the art.

In the process according to the invention the one or more co-monomers are capable of reacting with the ethylenically unsaturated monomer of general formula (IV), i.e. the one or more co-monomers together with the ethylenically unsaturated monomer of general formula (IV) may be polymerized to form a copolymer. Preferably, each co-monomer independently bears at least one ethylenically unsaturated group, which is preferably selected from the group consisting of —CH═CH$_2$, —C(CH$_3$)═CH$_2$ and —CH═CH—C$_1$-C$_6$-alkyl.

In a preferred embodiment of the process according to the present invention the one or more co-monomers comprise a co-monomer selected from the group consisting of (meth) acrylic acid, (meth)acrylic acid C$_1$-C$_{20}$-alkylester, (meth) acryl amide, ethylene, propylene, vinyl chloride, vinyl acetate, vinyl-C$_1$-C$_6$-alkyl-ether, vinyl pyrrolidone, methylstyrene, α-methylstyrene and styrene. Most preferred are (meth)acrylic acid, (meth)acrylic acid C$_1$-C$_{20}$-alkylester, styrene and mixtures thereof, in particular styrene.

In a preferred embodiment of the process according to the present invention the one or more co-monomers comprise a crosslinking co-monomer, i.e. a co-monomer having at least two functional groups capable of reacting with the ethylenically unsaturated groups of the ethylenically unsaturated monomer of general formula (IV). The skilled person is aware of suitable crosslinking monomers. Preferred crosslinking monomers are divinylbenzene, 1,4-diisopropenyl-benzene, 2-methyl-acrylic acid 2-(2-methyl-acryloyloxy)-ethyl ester, 2-methyl-acrylic acid 2-[2-(2-methyl-acryloyloxy)-ethoxy]-ethyl ester and longer homologues, 2-methyl-acrylic acid 2-[2-(2-methyl-acryloyloxy)-propoxy]-propyl ester and longer homologues, and 1,3,5-trivinyl-[1,3,5]triazinane-2,4,6-trione.

However, in another preferred embodiment the co-monomers do not comprise a crosslinking co-monomer.

In a preferred embodiment of the process according to the invention the ethylenically unsaturated monomer of general formula (IV) and the one or more co-monomers are polymerized in a weight ratio of from 1:4 to 3:2, i.e. the ethylenically unsaturated monomer of general formula (IV) amounts to 20-60 wt.-%, more preferably 30-50 wt.-%, based on the overall amount of all monomers (i.e. the total amount of the ethylenically unsaturated monomer of general formula (IV)+ the total amount of the one or more co-monomers).

Preferably, the one or more co-monomers comprise (meth) acrylic acid and the content of the (meth)acrylic acid in the overall amount of all monomers is between 1 and 10 wt.-%, more preferably between 2 and 6 wt.-%.

In a preferred embodiment of the invention the process comprises the step of polymerizing one or more co-monomers in the absence of the ethylenically unsaturated monomer of general formula (IV) thereby forming a core and the consecutive step of polymerizing the ethylenically unsaturated monomer of general formula (IV) and one or more co-monomers in order to form a shell on the core. Preferably, the core is formed by polymerizing styrene and the shell is formed by polymerizing a mixture of styrene, (meth)acrylic acid and the ethylenically unsaturated monomer of general formula (IV).

In a preferred embodiment of the process according to the invention the process comprises the further step of adding a hydrophilic compound to the ethylenically unsaturated monomer of general formula (IV) and the one or more co-monomers. Preferably, the hydrophilic compound is selected from the group consisting of polyethylene glycol (e.g. polyethylene glycol P 200 to P 6000), polypropylene glycol (e.g. polypropylene glycol P 200 to P 6000), acetone, ethyl methyl ketone, THF, dioxane, DMF, water soluble starch, water soluble cellulose and all types of cyclodextrin e.g. methylated cyclodextrin such as Cavasol® W7 M and mixtures of all these products.

The present invention also relates to the UV absorbing polymeric particles which are obtainable by the process described above.

Preferably, the polymeric particles have an average particle size of from 0.01 to 5 µm, more preferably 0.05 to 1 µm, most preferably 0.1 to 1.0 or 0.1 to 0.5 µm, in particular 0.15 to 0.4 µm.

The polymeric particles according to the present invention are capable of boosting the absorption of an UV filter which is contained in a sunscreen composition. Thus, when the polymeric particles according to the invention are combined with conventional UV filters, the overall UV absorption of the composition is preferably higher than the sum of the absorption of the isolated polymeric particles and the absorption of the isolated conventional UV filters (synergistic effect) and in addition some of the light is scattered or reflected and to pass once more the absorbing sunscreen layer. The boosting effect can be observed e.g. by measuring the UV transmission through a thin film of a sunscreen formulation, where the boosted formulation shows a smaller transmission value then the reference. It can also be determined by in vitro or in vivo SPF (sun protection factor) measurements.

The present invention also relates to a latex comprising the polymeric particles described above. A "latex" is defined as a colloidal dispersion of the polymers which are formed by emulsion polymerization. The polymeric particles according to the invention may be obtained from the latex by drying, i.e. evaporating the solvents from the latex. Preferably, the latex is lyophilized or spray dried to provide the polymeric particles.

Preferably, the latex according to the invention has a solids content of from 20 to 60 wt.-%, more preferably of from 30 to 50 wt.-%.

Preferably, the latex according to the invention comprises an aqueous suspension of polymeric particles having an average particle size of from 10 to 5,000 nm, preferably 100 to 1,000 nm, in particular 0.1 to 0.4 µm, such as 0.15 to 0.4 µm. The particles are preferably obtained by polymerizing an emulsion/a preheated emulsion of an organic and an aqueous phase. Preferably, the organic phase of the emulsion contains the ethylenically unsaturated monomer of general formula (IV); and the one or more co-monomers, such as styrene, (meth)acrylic acid and (meth)acrylic acid esters, and optionally one or more crosslinking monomers (as further co-monomers).

Preferably, the aqueous phase contains at least one initiator;

at least one emulsifier; and optionally a buffer to control the pH, such as a phosphate, citrate or bicarbonate buffer.

The present invention also relates to certain ethylenically unsaturated monomers according to general formula (IV) which can be advantageously incorporated in the polymer particles according to the invention.

Preferably, the ethylenically unsaturated monomer of general formula (IV) is one of the following compounds

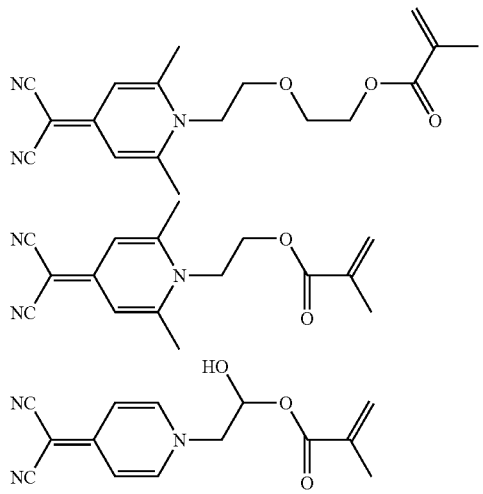

In another preferred embodiment, the ethylenically unsaturated monomer of general formula (IV) is a compound represented by any of general formulae (IV-A) to (IV-C)

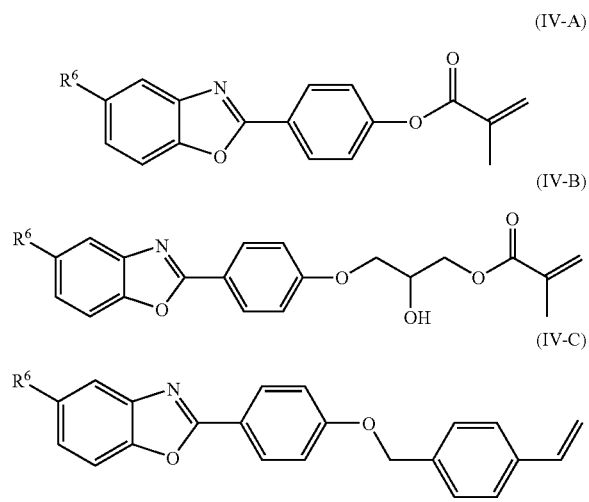

wherein $R^2$ is defined as above, more preferably —H or —$C_1$-$C_6$-alkyl. Most preferably, the ethylenically unsaturated monomer of general formula (IV) is one of the following compounds:

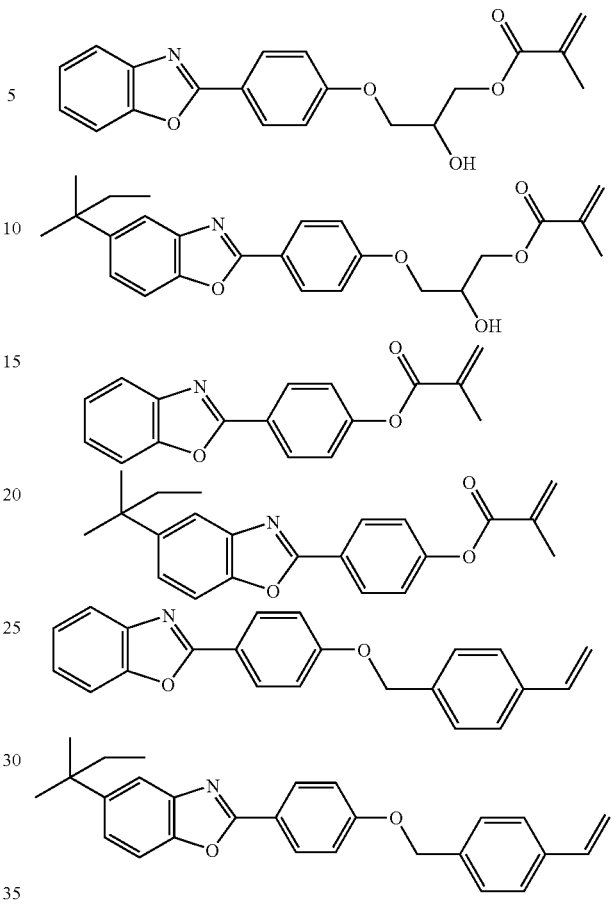

The polymeric particles and the latex according to the invention are useful as additive in sunscreens.

The present invention also relates to a process for boosting the UV absorption of an UV filter in a sunscreen composition comprising the step of adding the polymeric particles according to the invention to a sunscreen composition containing an UV filter.

The present invention also relates to a cosmetic composition comprising the polymeric particles or the latex described above as UV booster. Preferably, the "in vitro" sun protection factor (SPF), which may be measured by means of an Optometrix 290 Analyzer using 1.2 mg/cm$^2$ or by other suitable methods known in the art of the cosmetic composition on a PMMA support, is ≥3.0, more preferably ≥5.0, most preferably ≥7.0, in particular ≥7.5.

The compositions of the present invention are preferably cosmetic compositions or cosmetic preparations but they might also be pharmaceutical compositions.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York.

The compositions of the present invention contain the polymeric particles or the latexes UV booster in cosmetic preparations with cosmetically or pharmaceutically acceptable excipients or diluents. If nothing else is stated, the excipients, additives, diluents, etc. mentioned in the following are suitable for both pharmaceutical and cosmetic compositions.

If nothing else is stated, in this application parts and percentages are per weight and are based on the weight of the composition.

Preferably, the composition of the present invention contains the polymeric particles or the latex in a concentration of 0.001 to 50 wt.-%, more preferably 1 to 35 wt.-%, most preferably 4 to 30 wt.-% based on the weight of the composition.

The composition of the present invention preferably contains one or more UV absorbing chromophores (UV filters). These UV filters may be either covalently bound to a polymer but preferably are contained as separate compounds in the composition. The boosting effect of the polymeric particles according to the invention is particularly related to the UV absorption of these UV filters. Preferred UV filters are, e.g., compounds belonging to the groups of acrylates, p-aminobenzoates, camphor derivatives (such as of benzylidene camphor type), cinnamates, benzophenones, benzalmalonic acid esters, 2-(4-ethoxy anilinomethylene) propandioic esters, imidazole derivatives, salicylates, triazone derivatives, benzotriazol derivatives, dibenzoylmethanes, amino substituted hydroxybenzophenones, phenyl-benzimidazoles, anthranilates, phenyl-benzoxazoles, 1,4-dihydropyranes and 1,4-dihydropyridine derivatives, and others representing state of the art and known to those skilled in the art to be highly active.

Examples for acrylates include 2-ethylhexyl 2-cyano-3,3-diphenylacrylate (octocrylene, PARSOL® 340) and ethyl 2-cyano-3,3-diphenylacrylate.

Examples for p-aminobenzoates include 4-amino benzoic acid, 4-aminobenzoic acid-2,3-dihydroxypropylester, 4-(bis (2-hydroxypropyl)amino)benzoic acid ethyl ester, 4-(dimethyl-amino)benzoic acid-2-ethylhexylester (e.g. Eusolex® 6007) and ethoxylated 4-aminobenzoic acid ethyl ester (e.g. Uvinul® P25).

Examples for camphor derivatives include 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor and therephthalidene dicamphor sulfonic acid.

Examples for cinnamates include octyl methoxycinnamate (PARSOL® MCX), ethoxyethyl methoxycinnamate, diethanolamine methoxycinnamate (PARSOL® Hydro) and isoamyl methoxycinnamate.

Examples for benzophenones include benzophenone-3, benzophenone-4,2,2',4,4'-tetra-hydroxy-benzophenone and 2,2'-dihydroxy-4,4'dimethoxybenzophenone.

Examples for esters of benzalmalonic acid include di(2-ethylhexyl) 4-methoxybenzalmalonate.

Examples for esters of 2-(4-ethoxy anilinomethylene)propandioic acid include 2-(4-ethoxy anilinomethylene)propandioic acid diethyl ester as described in EP-A 895 776.

Examples for imidazole derivatives include 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts and diethanolamine salts.

Examples for salicylate derivatives include isopropylbenzyl salicylate, benzyl salicylate, butyl salicylate, octyl salicylate (NEO HELIOPAN OS), isooctyl salicylate or homomethyl salicylate (homosalate, HELIOPAN).

Examples for triazone derivatives include octyl triazone (UVINUL T-150), dioctyl butamido triazone (UVASORB HEB).

Examples for triazol derivatives include benzotriazoles such as 2-(2-hydroxy-5-methylphanyl)benzotriazole, 2,2'-methylene-bis-(6-(2H-benzotriazole-2-yl)-4-(1,1,3,3,-tetramethylbutyl)-phenol (TINOSORB M) as well as triazoles described in EP-A 893 119.

Examples for dibenzoylmethane derivatives include compounds such as 4-tert, butyl-4'-methoxydibenzoyl-methane (PARSOL® 1789), dimethoxydibenzoylmethane and isopropyldibenzoylmethane.

Examples for amino substituted hydroxybenzophenones include compounds such as 2-(4-Diethylamino-2-hydroxybenzoyl)-benzoic acid hexyl ester as described in EP-A 1 046 391.

Preferably, the compositions of the present invention are topical compositions, such as liquid or solid oil-in-water emulsions, water-in-oil emulsions, multiple emulsions, microemulsions, PET-emulsions, bickering emulsions, hydrogels, alcoholic gels, lipogels, one or multiphase solutions, foams, ointments, plasters, suspensions, powders, crèmes, cleanser, soaps and other usual compositions, which can also be applied by pens, as masks or as sprays.

The compositions of the invention can also contain usual cosmetic or pharmaceutical adjuvants and additives, such as preservatives/antioxidants, fatty substances/oils, water, organic solvents, silicones, thickeners, softeners, emulsifiers, sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into cosmetics or medicaments.

An additional amount of antioxidants/preservatives is generally preferred. Based on the invention all known antioxidants usually formulated into cosmetics or medicaments can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteine sulfoximine, buthionin sulfone, penta-, hexa-, heptathioninsulfoximine) in very low compatible doses (e.g. pmol to pmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-E-acetate), mixtures of nat. vitamin E, vitamin A and derivatives (vitamin-A-palmitate and -acetate) as well as coniferylbenzoat, rutinic acid and derivatives, α-glycosylrutin, ferulic acid, furfurylidenglucitol, carnosin, butylhydroxytoluene, butylhydroxyanisole, trihydroxybutyrophenone, urea and its derivatives, mannose and derivatives, zinc and derivatives (e.g. ZnO, ZnSO$_4$), selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the composition of the present invention. Preferably, one or more preservatives/antioxidants are present in an amount about 0.1 wt. % to about 1 wt. %.

Typically topical formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/ isostearic acid, polyglyceryl-6 hexaricinolate, polyglyceryl-4-oleate, polygylceryl-4oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/C$_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/C$_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the composition of the present invention. Preferably, about 0.1 wt. % to about 10 wt. % of emulsifiers are used.

The lipid phase of the topical compositions can advantageously be chosen from:
  mineral oils and mineral waxes;
  oils such as triglycerides of caprinic acid or caprylic acid, preferable castor oil;
  oils or waxes and other natural or synthetic oils, in an preferred embodiment esters of fatty acids with alcohols e.g. isopropanol, propylene glycol, glycerin or esters of fatty alcohols with carbonic acids or fatty acids;
  alkylbenzoates; and/or
  silicone oils such as dimethylpolysiloxane, diethylpolysiloxane, diphenyl-polysiloxane, cyclomethicones
and mixtures thereof.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropyl-myristate, isopropylpalmitate, isopropylstearate, isopropyloleate, n-butylstearate, n-hexyl-laureate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the topical compositions of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); a polar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in topical compositions of the present invention are isoeikosane; neopentylglycoldiheptanoate; propylenglycoldicaprylate/dicaprate; caprylic/capric/diglycerylsuccinate; butyleneglycol caprylat/caprat; C$_{12-13}$-alkyllactate; di-C$_{12-13}$ alkyltartrate; triisostearin; dipentaerythrityl hexacaprylat/hexacaprate; propyleneglycolmonoisostearate; tricaprylin; dimethylisosorbid. Especially beneficial is the use of mixtures C$_{12-15}$-alkylbenzoate and 2-ethylhexylisostearate, mixtures C$_{12-15}$-alkylbenzoate and isotridecylisononanoate as well as mixtures of C$_{12-15}$-alkylbenzoate, 2-ethylhexylisostearate and isotridecylisononanoate.

The oily phase of the compositions of the present invention can also contain natural vegetable or animal waxes such as bee wax, china wax, bumblebee wax and other waxes of insects as well as shea butter and cocoa butter.

A moisturizing agent may be incorporated into a topical composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of C$_{9-15}$-alcohols, isononyl iso-nonanoate, ethers such as polyoxypropylene butyl ethers and polyoxypropylene cetyl ethers, and C$_{12-15}$-alkyl benzoates, and mixtures thereof. The most preferred emollients are hydroxybenzoate esters, aloe vera, C$_{12-15}$-alkyl benzoates, and mixtures thereof. An emollient is present in an amount of about 1 wt. % to about 20 wt. % of the total weight of the composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a topical composition of the present invention such as glycerin, polypropylene glycol, polyethylene glycol, lactic acid, pyrrolidone carboxylic acid, urea, phopholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the preferred topical compositions of the present invention can contain the usual cosmetic or pharmaceutical additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or -monoethylether and analogue products, polymers, foam stabilizers; electrolytes and especially one or more thickeners. Thickeners that may be used in formulations of the present invention to assist in making the consistency of a product suitable include carbomer, siliciumdioxide, magnesium and/or aluminum silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the composition of the present invention.

The topical compositions of the invention can preferably be provided in the form of a lotion, a thickened lotion, a gel, a cream, a milk, an ointment, a powder or a solid tube stick and can be optionally be packaged as an aerosol and can be provided in the form of a mousse, foam or a spray. The compositions according to the invention can also be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The topical application is preferably at least once per day, e.g. two or three times a day. Usually it takes at least two days until the desired effect is achieved. However, it can take several weeks or even months until the desired effect is achieved.

The amount of the topical composition which is to be applied to the skin depends on the concentration of the active ingredients in the compositions and the desired cosmetic or pharmaceutical effect. For example, application can be such that a crème is applied to the skin. A crème is usually applied in an amount of 2 mg crème/cm$^2$ skin. The amount of the composition which is applied to the skin is, however, not critical, and if with a certain amount of applied composition the desired effect cannot be achieved, a higher concentration of the active ingredients can be used e.g. by applying more of the composition or by applying compositions which contain more active ingredient.

Regarding the kind of the topical preparation and the preparation of the topical preparations as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski K G, Augsburg).

The following examples exemplify the invention, but they should not be construed as limiting the scope of the invention.

EXAMPLE 1

4-(5-(1,1-Dimethyl-propyl)-2-benzoxazoyl)-phenyl methacrylic acid ester a) 2-Amino-4-(1,1-dimethyl-propyl)-phenol A 350 ml three necked reaction flask, equipped with a magnetic stirrer, a thermometer a $CO_2$ cooling bath, a reflux condenser and an oil bath were charged with 27.8 g (250 mmol) of 2-amino phenol (Fluka) suspended in 32.6 g (300 mmol) of 2-chloro-2-methyl butane in a nitrogen atmosphere. 87.5 ml of conc. $H_2SO_4$ were slowly added by means of a dropping funnel with strong cooling at −5° C. to −2° C. The HCl formed was entrapped in a flask filled with diluted NaOH. After stirring for 4 hours, the mixture was poured on 500 g of ice, neutralized with $Na_2CO_3$ to pH 9 and extracted with 3×500 ml of MTBE. The combined organic phases were dried with $Na_2SO_4$ and concentrated to yield 37.1 g of solid material which was washed in 75 ml of diisopropyl ether to yield 26.1 g (58%) of white crystals. M.p. 112-115° C.

b) 4-[5-(1,1-Dimethyl-propyl)-benzooxazol-2-yl]-phenol

A 350 ml three necked reaction flask, equipped with a mechanical stirrer, a thermometer a "wood metal" heating bath and a reflux condenser combined with a water separator were charged with 25.1 g (140 mmol) of 2-amino-4-(1,1-dimethyl-propyl)-phenol (see above), 19.3 g (140 mmol) of 4-hydroxy benzoic acid and 1.5 g of boric acid suspended in 140 ml of 1,2-dichlorobenzene under nitrogen atmosphere. This mixture was refluxed until two equivalents of water had separated (about 4 hours). When cold, 50 ml of diisopropylether were added and this mixture was filtered and the crystalline product was washed with diisopropylether and pentane and dried. 32.1 g (81%) of the product were obtained. M.p. 236-237° C.

c) 4-(5-(1,1-Dimethyl-propyl)-2-benzoxazoyl)-phenyl methacrylic acid ester

A 0.5 liter three necked reaction flask, equipped with a thermometer, a magnetic stirrer, a dropping funnel and a cooling bath was charged with 28.1 g (100 mmol) of 4-[5-(1,1-dimethyl-propyl)-benzooxazol-2-yl]-phenol (see above), 14.6 g (140 mmol) of triethylamine and 0.15 g of DMAP in 125 ml of $CH_2Cl_2$ under an atmosphere of nitrogen. After dissolution, the mixture was cooled to 0 to 4° C. and a solution of 10.55 g (98 mmol) of methacrylic acid chloride dissolved in 25 ml $CH_2Cl_2$ was slowly added in the above temperature range within 30 min. After stirring for further 30 min at 0° C. and 30 min at ambient temperature no starting material could be observed by TLC (thin layer chromatography). The mixture was washed successively with 100 ml of a saturated aqueous solution of $NaHCO_3$, with 2×100 ml of 5% aqueous citric acid and with saturated NaCl solution, dried over $Na_2SO_4$ and concentrated to form reddish crystals. It was re-crystallized first in diisopropyl ether and a trace of BHT and sucked off at −20° C. and dried to yield 22.0 g (63%) of fawn crystals; M.p. 96-97° C., UV (THF) 308 nm (27'623).

EXAMPLE 2

Preparation of Polymeric Particles Containing UV-Chromophores

A pre-emulsion was prepared by mixing an aqueous phase, prepared by dispersing the surfactant SDS (0.06 g) in water (8.37 g), with an organic phase containing styrene (10.45 g), methacrylic acid (0.67 g) and the UV-chromophore (4.48 g) 4-(5-(1,1-dimethyl-propyl)-2-benzoxazoyl)-phenyl methacrylic acid ester. The aqueous and the organic phase were mixed, vortexed, homogenized (Ultraturrax® homogenizer) and flushed with nitrogen. The pre-emulsion was stable for more than 24 hours.

A 100 ml reaction flask equipped with a stirrer, reflux condenser, thermometer and inlet tube for delivery from a peristaltic pump was placed in a water bath at 75° C. During nitrogen rinsing, a first initiator I-1 (0.92 ml $Na_2S_2O_8$, 1 molar) was added dropwise to the reaction flask containing water (1.9 ml), buffer (0.39 g, $NaHCO_3$), SDS (0.019 g) and a small amount of iron (II) sulfate. After 30 minutes the pre-emulsion and a second initiator I-2 (0.44 ml $Na_2S_2O_8$/1 molar) were separately added dropwise to the reaction flask under stirring at 420 rpm, using peristaltic pumps over a period of about 105 minutes. After terminating the addition, the reaction mixture was stirred for further 150 minutes and the bath temperature was increased up to 88° C. Subsequently, a third initiator I-3 (1.11 ml $Na_2S_2O_8$/0.1 molar) was added dropwise over a period of 45 minutes. After 180 minutes the reaction mixture was cooled to room temperature. Finally the particles were filtered through a 50 micrometer sieve.

EXAMPLE 3

Preparation of Core-Shell Polymeric Particles Containing UV-Chromophores

A pre-emulsion was prepared by mixing an aqueous phase prepared by dispersing the surfactant SDS (0.04 g) in water (6.62 g), with styrene (10.4 g). The aqueous phase and the organic phase were mixed, vortexed, homogenized (Ultraturrax® homogenizer) and flushed with nitrogen. The pre-emulsion was stable for more than 24 hours.

A 100 ml reaction flask equipped with a stirrer, reflux condenser, thermometer and inlet tube for delivery from a peristaltic pump was placed in a oil bath at 75° C. During nitrogen rinsing, a first initiator I-1 (0.92 ml $Na_2S_2O_8$/1 molar) was added to the reaction flask containing water (1.9 ml), buffer (0.39 g $NaHCO_3$), SDS (0.019 g) and a small amount of iron (II) sulfate. After 30 minutes the pre-emulsion and a second initiator I-2 (0.44 ml $Na_2S_2O_8$/1 molar) were separately added dropwise into the reaction flask under stirring, using peristaltic pumps over a period of about 105 minutes. After terminating the addition, the reaction mixture was stirred for further 150 minutes. Subsequently, the shell was formed by adding a mixture of styrene (2.5 g), methacrylic acid (0.82 g) and the UV-chromophore 4-(5-(1,1-dimethyl-propyl)-2-benzoxazoyl)-phenyl methacrylic acid ester (3.54 g) dropwise over a period of 85 minutes into the reaction flask. Simultaneously, initiator I-3 (1.1 ml $Na_2S_2O_8$/1 molar) was added dropwise and the reaction mixture was stirred for further 180 minutes before it was cooled to room temperature. Finally, the latex particles were filtered through a 50 micrometer sieve.

EXAMPLE 4

Preparation of Polymeric Particles Containing UV-Chromophores a) 4-(2-benzoxazoyl)-phenyl methacrylic acid ester

A 1 liter three necked reaction flask, equipped with a thermometer, a magnetic stirrer, a dropping funnel and an cooling bath was charged with 42.2 g (200 mmol) of 4-benzooxazol-2-yl-phenol (prepared by the method of Passerini; *J. Chem. Soc.;* 1954; 2256-7), 29.2 g (280 mmol) of triethylamine and 0.3 g of DMAP in 350 ml of $CH_2Cl_2$ under an atmosphere of nitrogen. After dissolution, the mixture was cooled to 0 to 4° C. and a solution of 21.1 g (196 mmol) of methacrylic acid chloride dissolved in 50 ml $CH_2Cl_2$ was slowly added in the above temperature range within 50 min. After stirring for further 30 min at 0° C. and 30 min at ambient temperature no starting material could be observed by TLC (thin layer chromatography). The mixture was washed successively with 200 ml of a saturated aqueous solution of $NaHCO_3$, with 2×100 ml of 5% aqueous citric acid and with saturated NaCl solution, dried over $Na_2SO_4$ and concentrated to form 53.6 g of a red material. This was re-crystallized first in MeOH and a trace of BHT and then in EtOAc to yield 36.3 g (66%) of fawn crystals; (HPLC 100% pure) m.p. 133-134° C., UV (THF) 302 nm (34'885).

b) Pre-Emulsion

A pre-emulsion was prepared by mixing an aqueous phase, prepared by dispersing the surfactant Sodiumlaurylsulfate (0.44 g) in water (30 g), with an organic phase containing styrene (23.5 ml), methacrylic acid (1.97 ml), Tween 80 (polyoxyethylene sorbitan monooleate/0.88 g), polyethylene glycol 400 (0.46 ml) and the above UV-chromophore (i.e. 4-(2-benzoxazoyl)-phenyl methacrylic acid ester/10.38 g). The aqueous and the organic phases were mixed by stirring followed by the aid of a "vibro mixer" at a temperature of 65° C. and flushed with nitrogen. This pre-emulsion was checked under a microscope and instantly used at a temperature of 65 to 70° C. for the emulsion polymerization.

c) Emulsion Polymerization

A four necked 200 ml reaction flask in an oil bath equipped with a magnetic stirrer, a heated dropping funnel of 250 ml content with dosage fine tuning facility, a thermometer and inlet tube for delivery from a peristaltic pump under argon atmosphere was charged with 33 mg of $NaHCO_3$, 57 mg of Tween 80, one crystal of $FeSO_4 \times 7H_2O$, 0.035 ml of polyethylene glycol 400, 0.1 ml of methacrylic acid in 5 ml of water and heated to 65° C. The above described emulsion and a separate solution of 1 g of sodium peroxy disulfate ($Na_2S_2O_8$) in 10 ml of water were added simultaneously and dropwise during 60 min constant addition. The emulsion coming from the dropping funnel was kept there at 65° C. and the persulfate solution was pumped through a flexible tube by the aid of the peristaltic pump. The reaction temperature went up to 71° C. and was later around 67° C. After additional 90 min, a solution of 0.076 g of $Na_2S_2O_8$ in 1 ml of water was added dropwise and the reaction temperature was kept at 65° C. for half an hour. The crude product was filtered through glass wool and a white slightly viscous filtrate of latex was obtained. UV (THF at pH 5.6) 350 nm (E=112). The average particle size was determined as 250 nm (Malvern at a pH of 5.6). Glass point at the same pH (thermogravimetric) 107° C.

A sample of the latex was precipitated by adding aq. NaCl and THF and dried to yield 42% content of solids in the latex, $M_w$ (by GPC with polystyrene as reference standard) 42'500 Dalton.

EXAMPLE 5 a) 2-Methyl-acrylic-acid-3-(4-benzoxazol-2-yl-phenoxy)-2-hydroxy-propyl ester

A 150 ml two necked reaction flask, equipped with a reflux condenser, a mechanical stirrer and an oil bath under nitrogen atmosphere was charged with 18.8 g (89 mmol) of 4-benzoxazol-2-yl-phenol (prepared by the method of Passerini; *J. Chem. Soc.;* 1954; 2256-7), 31.6 g (222 mmol) of glycidyl methacrylate, 0.29 of benzyl triethylammonium chloride and two crystals of 2-tert-butyl-4-methylphenol (BHT). The mixture was heated to 75° C. under stirring for two days, until the reddish suspension was fully dissolved to a dark red solution. The reaction was traced by TLC (in hexane/ethylacetate=1:1) until the starting material (Rf=0.65) had disappeared. Four new products were visible on the TLC plate, which were identified as the bis-methacrylic ester at the solvent front (Rf=0.86), the product in the middle (Rf=0.51), followed by a faint spot of the secondary ester 2-methyl-acrylic-acid-2-(4-benzoxazol-2-yl-phenoxy)-1-hydroxymethyl-ethyl ester) (Rf=0.44) and 3-(4-benzoxazol-2-yl-phenoxy)-propane-1,2-diol close to the start (Rf=0.075).

The product mixture was concentrated at the rotavap and chromatographed with hexane/ethylacetate=3:1 on Silica. The combined concentrated product fractions formed an orange crystalline material, which was washed in cold diisopropyl-ether/ethylacetate=9:1 to yield 14.6 g (46.6% of the theory in the first crop) of colorless crystals. M.p. 116.5-117° C. UV (THF) 308 nm (34'138). 4.86 g mother liquor (ca. additional 15%) was a mixture of the two mono-methacrylic esters of Rf=0.51 and 0.44. In some previous fractions about 18% of the bis-methycrylic ester (Rf=0.86) were isolated.

The same product was obtained in 50% yield without chromatography, when 10 mol % of triphenylphosphin hexylbromide catalyst were used instead of benzyl triethylammonium chloride and only 1.3 equivalents of glycidyl methacrylate, refluxing in toluene for 8 hours and the product was precipitated by the aid of heptane.

b) Pre-Emulsion

A pre-emulsion was prepared by mixing an aqueous phase, prepared by dispersing the surfactants Sodiumlaurylsulfate (2.6 g) in water (180 g), with an organic phase containing styrene (127.8 g), stabilized by 10 mg of BHT, methacrylic acid (12 g), Tween 80 (polyoxyethylene sorbitan monooleate/ 5.3 g), polyethylene glycol 400 (3.12 g) and the above UV-chromophore (2-methyl-acrylic-acid-3-(4-benzoxazol-2-yl-phenoxy)-2-hydroxy-propyl ester/62.2 g). The aqueous and the organic phases were mixed by stirring followed by the aid of a "vibro mixer" at a temperature of 65° C. and flushed with nitrogen. This pre-emulsion was checked under a microscope and instantly used at a temperature of 65 to 70° C. for the emulsion polymerization.

c) Emulsion Polymerization

A five necked 1 liter reaction flask equipped with a heating mantle, a mechanical stirrer, a heated dropping funnel of 500 ml content with dosage fine tuning facility, a thermometer and inlet tube for delivery from a peristaltic pump under argon atmosphere is charged with 0.2 g of $NaHCO_3$, 0.34 g of Tween 80, 0.02 g of $FeSO_4 \times 7H_2O$, 0.21 g of polyethylene glycol 400, 0.6 ml of methacrylic acid, 1.5 ml of latex product (pH=1.2) of a analogue prior reaction in 30 ml of water and heated to 70° C. The above described emulsion and a separate solution of 6 g of sodium peroxy disulfate ($Na_2S_2O_8$) in 60 ml of water were added simultaneously and dropwise during five hours constant addition. The emulsion coming from the dropping funnel was kept there at 65° C. and the persulfate solution was pumped in through a flexible tube by the aid of the peristaltic pump. After additional 45 min, a solution of 0.43 g of $Na_2S_2O_8$ in 6 ml of water was added dropwise over a period 30 min and at the same time the reaction temperature was raised to 85° C. for one hour. The crude product was filtered through glass wool and 400 g of a white slightly viscous filtrate of latex were obtained. UV (THF at pH 5.6) 350 nm (E=132). The average particle size at pH 5.6 was determined as 250 nm (Malvern). Glass point of pH 5.6 material (thermogravimetric) 102° C. The photostability of this product was measured according to Berset et. al.; *Int. J. Cosmetic Science* 18:167-177 (1996) using the latex without further dissolution as liquid phase. The product was found to be photostable.

A sample of the latex was precipitated by adding aqueous NaCl and THF and dried to yield 39.4% content of solids in the latex, UV (THF) 350 nm (E=267). $M_w$ (by GPC with polystyrene as reference standard) 37,000 Dalton.

A further sample of this latex was lyophilized to give a free flowing white powder, which could also be used for the preparation of cosmetic creams.

EXAMPLE 6 a) Pre-Emulsion

A pre-emulsion was prepared by mixing an aqueous phase, prepared by dispersing the surfactant Sodiumlaurylsulfate (0.44 g) in water (35 g), with an organic phase containing styrene (23.5 ml), methacrylic acid (2.73 ml), 1,4-Divinyl benzene (0.46 ml), Tween 80 (polyoxyethylene sorbitan monooleate/0.88 g), polyethylene glycol 400 (0.46 ml) and the above UV-chromophore from example 4a (i.e. 4-(2-benzoxazoyl)-phenyl methacrylic acid ester/10.38 g). The aqueous and the organic phases were mixed by stirring followed by the aid of a "vibro mixer" at a temperature of 65° C. and flushed with nitrogen. This pre-emulsion was checked under a microscope and instantly used at a temperature of 65 to 70° C. for the emulsion polymerization.

b) Emulsion Polymerization

A four necked 200 ml reaction flask in an oil bath equipped with a magnetic stirrer, a heated dropping funnel of 250 ml content with dosage fine tuning facility, a thermometer and two inlet tubes for delivery from a peristaltic pump under argon atmosphere was charged with 0.2 ml of 2n NaOH, 60 mg of Tween 80, one crystal of $FeSO_4 \times 7H_2O$, 0.04 ml of polyethylene glycol 400, 0.1 ml of methacrylic acid in 10 ml of water and heated to 65° C. The above described emulsion, a separate solution of 9.45 ml of 2n NaOH and a second separate solution of 1 g of sodium peroxy disulfate ($Na_2S_2O_8$) in 10 ml of water were added simultaneously and dropwise during 60 min constant addition in such a way that the addition of the three solutions was completed at the same time. The emulsion coming from the dropping funnel was kept there at 65° C. The persulfate solution and the NaOH solution were pumped in parallel through a flexible tube each by the aid of the peristaltic pump. The reaction temperature went up to 71° C. and was later around 67° C. After additional 90 min, a solution of 0.076 g of $Na_2S_2O_8$ in 1 ml of water was added dropwise and the reaction temperature was kept at 65° C. for half an hour. The crude product was filtered through glass wool and a white slightly viscous filtrate of latex was obtained (pH was 5.0). The average particle size was determined as 300 nm (Malvern at a pH of 5.6).

This latex material was lyophilized to give a free flowing white powder.

EXAMPLE 7

Preparation of an Amphisol Formulation Containing 10% Solid Material of the Latex as an O/W Sunscreen

| wt.-% | compound | chemical name |
|---|---|---|
| Part A | | |
| 2 | Amphisol K (Givaudan) | potassium cetylphosphate |
| 2 | cetyl alcohol | |
| 3 | Estol GGM 3650 | glyceryl myristate |
| 10 | Myritol 318 | caprylic/capric triglyceride |
| 7 | Tegasoft TN | $C_{10-15}$ alkylbenzoate |
| 0.1 | BHT | butyl hydroxy toluene |
| Part B | | |
| 42.37 | water deionized | |
| 5 | propylene glycol | |
| 0.1 | Edeta BD | EDTA |
| 27.03 | latex solution of example 4 | |
| Part C | | |
| 0.2 | NaOH (30%) | |
| Part D | | |
| 1 | Phenonip | phenoxyethanol, alkyl-paraben mixture |

The ingredients of part were combined, stirred and adjusted to the desired pH by means of part C. Parts A and B were heated separately to 80° C. Part A was added to part B under stirring and homogenized for 30 seconds at 9500 rpm. The mixture was cooled down to 40° C. under stirring and added part D. The pH was monitored.

The "in vitro" sun protection factor (SPF) was measured, using an Optometrix 290 Analyzer, 1.2 mg/cm$^2$ of the above formulation on a PMMA support. The SPF was found to be 7.9.

EXAMPLE 8

Preparation of a Brij Formulation Containing 10% Solid Material of the Latex as an O/W Sunscreen

| wt.-% | compound | chemical name |
|---|---|---|
| Part A | | |
| 2 | Brij 721 | Steareth-21 |
| 2 | Brij 21 | Steareth-2 |
| 1 | Lanette 18 | stearyl alcohol |
| 1 | Lanette 22 | behenyl alcohol |
| 1 | cetyl alcohol | |
| 13 | Miglyol 812 N | caprylic/capric triglyceride |
| 3 | Arlamol HD | isohexadecane |
| 0.05 | BHT | butyl hydroxy toluene |
| 1 | Phenonip | phenoxyethanol, alkyl-paraben mixture |
| Part B | | |
| 46.77 | water deionized | |
| 2 | glycerin | |
| 0.1 | Edeta BD | EDTA |
| 0.05 | KOH (10% sol.) | |
| 27.03 | latex solution of example 4 | |

The ingredients of part B were combined under stirring. Parts A and B were heated separately to 80° C. Part A was added to part B under stirring and homogenized for 30 seconds at 9500 rpm. The mixture was cooled down to ambient temperature and the pH monitored.

EXAMPLE 9

Preparation of a Brij Formulation Containing 5% Solid Material of the Lyophilized Latex

| wt.-% | compound | chemical name |
|---|---|---|
| Part A | | |
| 2 | Brij 721 | Steareth-21 |
| 2 | Brij 21 | Steareth-2 |
| 1 | Lanette 18 | stearyl alcohol |
| 1 | Lanette 22 | behenyl alconol |
| 1 | cetyl alcohol | |
| 13 | Miglyol 812 N | caprylic/capric triglyceride |
| 3 | Arlamol HD | isohexadecane |
| 0.05 | BHT | butyl hydroxy toluene |
| 1 | Phenonip | phenoxyethanol, alkyl-paraben mixture |
| Part B | | |
| 68.51 | water deionized | |
| 2 | glycerin | |
| 0.1 | Edeta BD | EDTA |
| 0.34 | KOH (10% sol.) | |
| 5 | lyophilized latex powder of example 4 | |

The ingredients of part B were combined under stirring. Parts A and B were heated separately to 80° C. part A was added to part B under stirring and homogenized for 30 seconds at 9500 rpm. The mixture was cooled down to ambient temperature and the pH was monitored.

EXAMPLE 10

Boosting Effect

Comparison of a standard formulation (32)
a) with the same formulation containing 5% Latex (30)
b) with the same formulation containing 2% Latex (31)
c) with the same formulation containing 6% Sunspheres PGL (33)
d) with the same formulation containing 2% Uvinul TiO2 (34)
e) with the same formulation containing 2% additional Parsol MCX (35)
f) with the same formulation containing 5% additional Parsol MCX (36)

| | Formula Nr: | 30% | 31% | 32% | 33% | 34% | 35% | 36% |
|---|---|---|---|---|---|---|---|---|
| A) | Amphisol A | 2.00 | 2.00 | 2.00 | 2.00 | 2.00 | 2.00 | 2.00 |
| | Cetyl Alcohol | 1.00 | 1.00 | 1.00 | 1.00 | 1.00 | 1.00 | 1.00 |
| | Estol GMM 3650 (Glyceryl Myristate) | 3.00 | 3.00 | 3.00 | 3.00 | 3.00 | 3.00 | 3.00 |
| | Parsol 1789 | 2.00 | 2.00 | 2.00 | 2.00 | 2.00 | 2.00 | 2.00 |
| | Parsol MCX | 4.00 | 4.00 | 4.00 | 4.00 | 4.00 | 4.00 | 4.00 |
| | Parsol MCX | | | | | | 2.00 | 5.00 |
| | Parsol 340 | 4.00 | 4.00 | 4.00 | 4.00 | 4.00 | 4.00 | 4.00 |
| | Uvinul TIO2 | | | | | 2.00 | | |
| | Myritol 318 | 5.00 | 5.00 | 5.00 | 5.00 | 5.00 | 5.00 | 5.00 |
| | Finsolv TN | 3.00 | 3.00 | 3.00 | 3.00 | 3.00 | 3.00 | 3.00 |
| | BHT | 0.05 | 0.05 | 0.05 | 0.05 | 0.05 | 0.05 | 0.05 |
| | Phenonip | 0.80 | 0.80 | 0.80 | 0.80 | 0.80 | 0.80 | 0.80 |
| B) | Water | 29.73 | 32.65 | 64.55 | 58.73 | 62.81 | 62.73 | 59.81 |
| | Propylene Glycol | 5.00 | 5.00 | 5.00 | 5.00 | 5.00 | 5.00 | 5.00 |
| | Edeta BD | 0.10 | 0.10 | 0.10 | 0.10 | 0.10 | 0.10 | 0.10 |
| | Carbopol Ulterz 21 | 0.30 | 0.30 | 0.30 | 0.30 | 0.30 | 0.30 | 0.30 |
| | Trometamin 25% sol | 5.02 | 5.10 | 5.20 | 5.02 | 4.94 | 5.02 | 4.94 |
| C) | water | 30.00 | 30.00 | | | | | |
| | Latex powder of example 6 | 5.00 | 2.00 | | | | | |
| D) | Sunsphere PGL | | | | 6.0 | | | |
| | | 100.0 | 100.0 | 100.0 | 100.0 | 100.0 | 100.0 | 100.0 |

30 and 31: C): Disperse Lyophilisat in water under stirring at 60° C. for 1 hour. Heat part A and B separately to 80° C. Add part A to B and homogenize 25 seconds at 13000 rpm. Add C) to AB under stirring at 60° C., homogenize 45 sek at 13000 rpm and cool down under stirring. 32: Heat A and B separately to 80° C. and mix under stirring, let cool down under stirring and homogenize 45 sek. at 13000 rpm. 33: Heat A and B separately to 80° C. mix and cool down under stirring, add D under stirring and homogenize 45 sek. at 13000 rpm. 34: Heat A (without Uvinul) and B separately to 80° C. Add Uvinul to A and homogenize 20 sek at 13000 rpm, add B and cool down under stirring. Homogenize for 45 sek. at 13000 rpm. 35 and 36: proceed in accordance with the procedure of 32.

The UV Transmission of the formulations 30 to 36 was measured with a Perkin Elmer Lambda 650S UV/Vis Spectrometer through a 8 micrometer cuvette:

The table shows a mean transmission values of three measurements at 300 nm and 350 nm and the respective boosting factors in comparison to the reference formula 32

| in % | at 300 nm Transmission | at 350 nm Transmission |
|---|---|---|
| reference | 24.1 | 34.3 |
| Formula 32 | 18.3 | 28.9 |
| | 25.5 | 36.5 |
| mean value | 22.6 | 33.2 |
| 2% Latex | 5.8 | 11.6 |
| Formula 31 | 7.5 | 12.8 |
| | 6.6 | 9.7 |
| mean value | 6.6 | 11.4 |
| boosting factor | 3.41 | 2.92 |
| 5% Latex | 0.51 | 0.7 |
| Formula 30 | 1.7 | 2.6 |
| | 2 | 3 |
| mean value | 1.4 | 2.1 |
| boosting factor | 16.13 | 15.83 |
| additional | 8.6 | 14.8 |
| 2% Parsol MCX | 10.3 | 17.2 |
| Formula 35 | 8.9 | 16.2 |
| mean value | 9.3 | 16.1 |
| boosting factor | 2.44 | 2.07 |
| additional | 6.1 | 11.1 |

-continued

| in % | at 300 nm Transmission | at 350 nm Transmission |
|---|---|---|
| 5% Parsol MCX | 5.9 | 10.9 |
| Formula 36 | 4.1 | 8.3 |
| mean value | 5.4 | 10.1 |
| boosting factor | 4.22 | 3.29 |
| 6% Sunspheres | 8.8 | 13.6 |
| Formula 33 | 10.3 | 14.9 |
| | 7.7 | 12.2 |
| mean value | 8.9 | 13.6 |
| boosting factor | 2.53 | 2.45 |
| 2% $TiO_2$ | 6.2 | 11.4 |
| Formula 34 | 5.7 | 9.7 |
| | 3.7 | 6.8 |
| mean value | 5.2 | 9.3 |
| boosting factor | 4.35 | 3.57 |

EXAMPLE 11

A sample of the standard formulation (32) and the same formulation containing 2% Latex (31) of example 10 was applied onto the skin of the human forearm. The standard formulation (32) created a shiny appearance of the skin, whereas the formulation containing 2% latex (31) generated velvet-like appearance and smoothened and flattened the skin.

The invention claimed is:

1. A process for boosting ultraviolet (UV) absorption of a UV filter in a UV sunscreen composition comprising adding to the sunscreen composition polymeric particles comprising at least one chromophore having a UV absorption maximum at $\lambda_{max} \geq 275$ nm covalently bound thereto, wherein the chromophore comprises a moiety according to general formula (III)

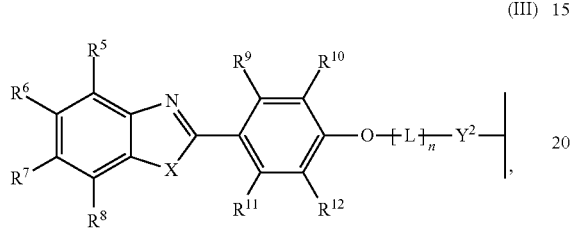

wherein ⇁ denotes a covalent bond to the polymeric particle, and wherein, $R^5, R^6, R^7, R^8, R^9, R^{10}, R^{11}, R^{12}$ are independently selected from —H, —F, —Cl, —CN, —CF$_3$, —N$_3$, —NO, —NO$_2$, —OH, —OCO—C$_1$-C$_6$-alkyl, —CO$_2$H, —SO$_3$H, —CO$_2$—C$_1$-C$_6$-alkyl, —S(O)$_k$—C$_1$-C$_6$-alkyl wherein index k is 0, 1 or 2; —CO—C$_1$-C$_6$-alkyl, —NH$_2$, —NH—C$_1$-C$_6$-alkyl, —N(C$_1$-C$_6$-alkyl)$_2$, —NHCO—C$_1$-C$_6$-alkyl, —C$_1$-C$_{20}$-alkyl wherein optionally 1, 2 or 3 methylene groups are replaced by —O—, —C$_3$-C$_7$-cycloalkyl; methenyl which may optionally be substituted with $R^a$ and $R^b$ independently selected from —Cl, —CN, —CO$_2$—C$_1$-C$_6$-alkyl and —O—C$_1$-C$_6$-alkyl; —C$_2$-C$_{20}$-alkenyl, —C$_2$-C$_{20}$-alkynyl, —C$_6$-C$_{10}$-aryl, —C$_3$-C$_9$-heteroaryl, —C$_7$-C$_{20}$-alkylaryl wherein optionally 1, 2 or 3 methylene groups are replaced by —O—, —CO—C$_6$-C$_{10}$-aryl or —C$_5$-C$_{20}$-alkylheteroaryl, L is a linker unit, $Y^2$ is —O—; —CO—; —CO$_2$—; —OCO—; —NR'CO— wherein R' is —H or —C$_1$-C$_6$-alkyl; —C$_1$-C$_6$-alkylene-; or -phenylene- substituted with $R^9$, $R^{10}$, $R^{11}$ and $R^{12}$ wherein each of $R^9$, $R^{10}$, $R^{11}$ and $R^{12}$ is H, n is an integer of 0 to 10, and X is —S—, —O— or —NR'''—, wherein R''' is —H or —C$_1$-C$_{20}$-alkyl.

2. The process according to claim 1, wherein $\lambda_{max} \geq 290$ nm.

3. The process according to claim 1, wherein the chromophore comprises a moiety selected from the group consisting of acrylates, p-aminobenzoates, camphor derivatives, cinnamates, benzophenones, benzalmalonic acid esters, 2-(4-ethoxy anilinomethylene)-propandioic esters, imidazole derivatives, salicylates, triazone derivatives, benzotriazol derivatives, dibenzoylmethanes, amino substituted hydroxybenzophenones, phenyl-benzimidazoles, anthranilates, phenyl-benzoxazoles, 1,4-dihydropyranes and 1,4-dihydropyridine derivatives.

4. The process according to claim 1, wherein the polymeric particles have an average particle size that is within the range of from 0.01 to 5 µm.

5. The process according to claim 1, wherein index n is 1 or 2 and L is —C$_2$-C$_6$-alkylene-O— or —C$_2$-C$_6$-alkylene-NH—, and wherein the carbon atoms of each alkylene-group may be optionally substituted with one, two or three hydroxy groups.

6. The process according to claim 1, wherein index n is 0.

* * * * *